US009655948B1

(12) United States Patent
Koob et al.

(10) Patent No.: US 9,655,948 B1
(45) Date of Patent: May 23, 2017

(54) NON-SURGICAL, LOCALIZED DELIVERY OF COMPOSITIONS FOR PLACENTAL GROWTH FACTORS

(71) Applicant: MiMedx Group, Inc., Marietta, GA (US)

(72) Inventors: Thomas J. Koob, Marietta, GA (US); Rebeccah J. C. Brown, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 14/157,444

(22) Filed: Jan. 16, 2014

Related U.S. Application Data

(60) Provisional application No. 61/956,185, filed on Jan. 17, 2013.

(51) Int. Cl.
A61K 9/19 (2006.01)
A61K 35/50 (2015.01)
A61K 38/18 (2006.01)

(52) U.S. Cl.
CPC .......... *A61K 38/1866* (2013.01); *A61K 9/19* (2013.01); *A61K 35/50* (2013.01); *A61K 38/18* (2013.01)

(58) Field of Classification Search
CPC .............. A61K 2300/00; A61K 35/50; A61K 38/1866; A61K 38/1709; A61K 31/728; A61K 38/18; A61K 38/00; A61K 45/06; A61K 9/14; A61K 9/16; A61K 9/19
See application file for complete search history.

(56) References Cited

U.S. PATENT DOCUMENTS

| 2,694,914 | A | 11/1954 | Glover, Jr |
| 4,564,368 | A | 1/1986 | Sawyer et al. |
| 4,745,771 | A | 5/1988 | Linner et al. |
| 4,968,325 | A | 11/1990 | Black et al. |
| 5,118,867 | A | 6/1992 | Bahrmann et al. |
| 5,284,655 | A | 2/1994 | Bogdansky et al. |
| 6,030,635 | A | 2/2000 | Gertzman et al. |
| 7,311,904 | B2 | 12/2007 | Hariri |
| 7,311,905 | B2 | 12/2007 | Hariri |
| 8,067,044 | B2 | 11/2011 | Henry et al. |
| 8,153,162 | B2 | 4/2012 | Tseng et al. |
| 8,323,701 | B2 | 12/2012 | Daniel et al. |
| 8,357,403 | B2 | 1/2013 | Daniel et al. |
| 8,372,439 | B2 | 2/2013 | Daniel et al. |
| 2002/0123141 | A1 | 9/2002 | Hariri |
| 2002/0160510 | A1 | 10/2002 | Hariri |
| 2003/0032179 | A1 | 2/2003 | Hariri |
| 2003/0187515 | A1 | 10/2003 | Hariri et al. |
| 2004/0048796 | A1 | 3/2004 | Hariri et al. |
| 2006/0140913 | A1 | 6/2006 | Bhatia |
| 2006/0154860 | A1 | 7/2006 | Ceradini et al. |
| 2006/0210532 | A1 | 9/2006 | Carmeliet et al. |
| 2006/0233850 | A1 | 10/2006 | Michal |
| 2007/0021704 | A1 | 1/2007 | Hariri et al. |
| 2007/0021762 | A1 | 1/2007 | Liu et al. |
| 2007/0071740 | A1* | 3/2007 | Tseng et al. ............... 424/94.1 |
| 2007/0202189 | A1 | 8/2007 | Ahlfors |
| 2007/0248575 | A1 | 10/2007 | Connor et al. |
| 2007/0299043 | A1 | 12/2007 | Hunter et al. |
| 2008/0046095 | A1 | 2/2008 | Daniel |
| 2008/0050347 | A1 | 2/2008 | Ichim |
| 2008/0069895 | A1 | 3/2008 | Liu et al. |
| 2008/0131966 | A1 | 6/2008 | Hariri |
| 2008/0181967 | A1 | 7/2008 | Liu et al. |
| 2008/0233552 | A1 | 9/2008 | Ma et al. |
| 2009/0012629 | A1 | 1/2009 | Yao et al. |
| 2009/0142831 | A1 | 6/2009 | Hariri |
| 2009/0291891 | A1 | 11/2009 | Neufeld |
| 2010/0028849 | A1 | 2/2010 | Shelby et al. |
| 2010/0104539 | A1 | 4/2010 | Daniel et al. |
| 2010/0136114 | A1 | 6/2010 | Mao |
| 2010/0143312 | A1 | 6/2010 | Hariri et al. |
| 2010/0178297 | A1 | 7/2010 | Carmeliet et al. |
| 2010/0209408 | A1 | 8/2010 | Stephen et al. |
| 2010/0260847 | A1 | 10/2010 | Hariri |
| 2010/0272679 | A1 | 10/2010 | Penn et al. |
| 2010/0272782 | A1 | 10/2010 | Owens et al. |
| 2011/0044997 | A1 | 2/2011 | Rankin et al. |
| 2011/0177150 | A1 | 7/2011 | Pathak et al. |
| 2011/0307059 | A1 | 12/2011 | Young et al. |
| 2012/0010708 | A1 | 1/2012 | Young et al. |
| 2012/0030963 | A1 | 2/2012 | Durance et al. |
| 2012/0078378 | A1 | 3/2012 | Daniel et al. |

(Continued)

FOREIGN PATENT DOCUMENTS

| CN | 101433556 A | * | 5/2009 |
| EP | 0431479 A1 | | 6/1991 |
| KR | 10/1991/0011272 | | 8/1991 |

(Continued)

OTHER PUBLICATIONS

O'Keefe et al., Cell Physiol. Sep. 1985;124(3):439-445.*
U.S. Appl. No. 13/647,308, filed Oct. 8, 2012, Daniel et al.
U.S. Appl. No. 13/688,091, filed Nov. 28, 2012, Spencer et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/744,332, filed Jan. 17, 2013, Pringle et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,753, filed Mar. 15, 2013, Koob et al.
U.S. Appl. No. 13/815,784, filed Mar. 15, 2013, Koob et al.
U.S. Appl. No. 13/815,873, filed Mar. 15, 2013, Brown et al.
U.S. Appl. No. 13/963,984, filed Aug. 9, 2013, Daniel et al.
U.S. Appl. No. 13/967,326, filed Aug. 14, 2013, Koob et al.
U.S. Appl. No. 13/983,301, filed Aug. 1, 2013, Morse et al.
U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Product Brochure (2011).

(Continued)

Primary Examiner — Daniel C Gamett
(74) Attorney, Agent, or Firm — Alston & Bird LLP

(57) ABSTRACT

Described herewith are compositions comprising placental growth factors and methods for non-surgical, localized delivery thereof. The composition is delivered to a diseased or injured organ and/or body part and is formulated in a manner which allows for localized retention of the composition at the site of delivery.

11 Claims, No Drawings

(56) References Cited

U.S. PATENT DOCUMENTS

2013/0095060 A1* 4/2013 Hsieh et al. ............... 424/85.1
2013/0230561 A1   9/2013 Daniel et al.

FOREIGN PATENT DOCUMENTS

| KR | 10/1991/0011727 | | 8/1991 | |
|---|---|---|---|---|
| KR | 0110588 A | * | 11/2001 | |
| SU | WO 9012584 A1 | * | 11/1990 | ............. A61K 35/50 |
| WO | WO-01/08716 A1 | | 2/2001 | |
| WO | WO-2005/017165 | | 2/2005 | |
| WO | WO-2009/033160 A1 | | 3/2009 | |
| WO | WO-2009/048908 | | 4/2009 | |
| WO | WO-2009/132186 A1 | | 10/2009 | |
| WO | WO-2010/029344 A2 | | 3/2010 | |
| WO | WO-2012/112410 A2 | | 8/2012 | |
| WO | WO-2012/112417 A2 | | 8/2012 | |
| WO | WO-2012/112441 A1 | | 8/2012 | |
| WO | WO-2015/031681 A1 | | 3/2015 | |
| WO | WO-2015/038477 A1 | | 3/2015 | |
| WO | WO-2015/109329 A1 | | 7/2015 | |
| WO | WO-2016/040385 A1 | | 3/2016 | |
| WO | WO-2016/128916 A1 | | 8/2016 | |

OTHER PUBLICATIONS

Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Koob et al., "Biological properties of dehydrated human amnion-chorion composite graft: implications for chronic wound healing", International Wound Healing, 2013, 10(5):493-500.
Mayfield et al., "Watertight closure of spinal dura mater: Technical note," J. Neurosurg., (1975), 43(5):639-640.
PCT International Preliminary Report on Patentability for copending PCT Application No. PCT/US2012/024798, dated Feb. 1, 2013.
PCT International Search Report and Written Opinion for copending PCT Application No. PCT/US2013/064146, dated Jan. 9, 2014.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2013/054322, dated Oct. 22, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
PCT International Search Report for copending PCT Application No. PCT/US2012/024798, dated Jun. 20, 2012.
Tao, et al., "Implantation of amniotic membrane to reduce postlaminectomy epidurla adhesions," Eur. Spine. J., (2009), 18:1202-1212.
U.S. Appl. No. 14/157,445, filed Jan. 16, 2014, Koob, et al.
Inokuma et al.,CTACK/CCL27 Accelerates Skin Regeneration via Accumulation of Bone Marrow-Derived Keratinocytes, Stem Cells, 2006, 24:2810-2916.
MyBioSource/www.mybiosource.com/prods/Recombinant-Protein/ CCL27-CTACK/datasheet.php?products-id-444088> (Accessed Jun. 9, 2015).
Nibbs et al., CCL27/Pesky: A Novel Paradigm for Chemokine Function, 2003, Expert Opin. Biol. Ther., 3(1):15-22.
PCT International Preliminary Report of Patentability for PCT Patent Application PCT/US2013/064146, dated Sep. 25, 2014.
Zaja-Milatovic et al., CXC Chemokines and Their Receptors: A case for a significant Biological Role in Cutaneous Wound Healing, Histol. Histopathol., Nov. 2008, 23(11):1399-1407.
Ahmed et al., "Regulation of Placental Vascular Endothelial Growth Factor (VEG F) and Placenta Growth Factor (PlGF) and Soluble Flt-1 by Oxygen—A Review", Placenta (2000), 21(14A):516-524.
Coulomb-L'Hermine et al., "Letter to the Editor. SDF-1 Production by Placental Cells: A Potential Mechanism of Inhibition of Mother-to-Fetus HIV Transmission", AIDS Research and Human Retroviruses (2000), 16(11):1097-1098.
Rabbany et al., "Continuous Delivery of Stromal Cell-Derived Factor-1 From Alginate Scaffolds Accelerates Wound Healing", Cell Transplantation (2010), 19:399-408.
PCT International Search Report and Written Opinion for related PCT Application No. PCT/US2016/050382, dated Nov. 14, 2016.

* cited by examiner

NON-SURGICAL, LOCALIZED DELIVERY OF COMPOSITIONS FOR PLACENTAL GROWTH FACTORS

CROSS-REFERENCE TO RELATED APPLICATIONS

This application claims the benefit under 35 U.S.C. §119 (e) to U.S. provisional application Ser. No. 61/956,185 which was converted from U.S. nonprovisional application Ser. No. 13/744,331, filed Jan. 17, 2013; all of which are incorporated hereby by reference in their entirety.

BACKGROUND OF THE INVENTION

Field of the Invention

This invention is directed, in part, to compositions comprising placental growth factors and methods for non-surgical, localized delivery thereof. In one embodiment, the composition is delivered to a diseased or injured organ and/or body part and is co-delivered with an agent which allows for localized retention of the composition at the site of delivery.

State of the Art

Heretofore, modified placental tissue has been used to treat a diseased or injured internal organ or body part. However, such use has been limited by the amount of tissue available and the size of the organ. As a general rule, the minimum amount of modified placental tissue to elicit the desired result has been used. For example, in one embodiment, the placental tissue is used as a barrier layer between organs so as to prevent adhesion formation. See, for example, U.S. Patent Application Publication No. 2010/0104539.

The in vivo placement of a modified placental tissue also requires an invasive process whereby the placement requires an incision which typically accompanies surgery. However, injectable solutions containing a suspension of placental tissue recently have been used to provide for non-invasive delivery of the placental tissue. While this approach allows for direct delivery of the placental tissue to the in vivo delivery site, the size and amount of the placental tissue so delivered is limited by the width of the injection needle and the volume delivered.

SUMMARY OF THE INVENTION

This invention is based, in part, on the discovery that placental growth factors can be extracted from modified placental tissue in sufficient quantities so as to provide for an aqueous composition comprising growth factors optionally without the need to form a suspension with modified placental tissue particles. In one embodiment, the placental growth factors are extracted from modified placental tissue using a biocompatible buffer or solution, such as a saline solution. Preferably, the saline solution is a NaCl solution having a concentration of less than or about 0.5 M, less than or about 1.0 M, less than or about 1.5 M, or less than or about 2.0 M. Alternatively, the saline solution is a NaCl solution having a concentration of less than or about 1%, less than or about 5%, less than or about 10%, or less than or about 15%.

This invention is also based on the discovery that localized delivery of the composition can be achieved by co-delivery in the solution or suspension of an agent which allows for localized retention of the solution or suspension at the site of delivery. Such agents include thixotropic agents, phase changing agents, and the like. When co-delivered, these agents form a viscous or gel-like bioerodable or biodegradable mass in vivo which limits transport away from the site of delivery and allows for the diffusion of the growth factors from the mass formed over a period of time.

Accordingly, in one aspect of this invention there is provided a composition comprising a sufficient amount of placental growth factor to treat a diseased or injured organ and a body part wherein said composition forms a localized mass when applied to or proximate to said diseased or injured organ or body part.

In another aspect of this invention, the composition contains modified placental tissue particles as defined herein. In another embodiment, the composition is free of modified placental tissue particles.

In another aspect, there is provided a method for preparing a composition for localized delivery of placental growth factors, which method comprises combining an aqueous suspension of placental tissue particles or an aqueous solution of placental growth factors with a sufficient amount of an agent which allows for localized retention of the solution or suspension at the site of delivery. Such agents include thixotropic agents, phase changing agents, and the like.

The biocompatible thixotropic agent is selected, by way of example only, from hyaluronic acid, collagen, thrombin gels, fibrin gels and fibrin glues. In another embodiment, the phase changing agent is a gel forming agent, such as a Pluronic® (e.g., a copolymer of oxyethylene and oxypropylene). Preferably, any polymer used as a thixotropic agent or a phase changing agent is bioerodible. In yet another embodiment, the body part is selected from the group consisting of skin, mucosal membrane, gum adjacent to teeth, bone, cartilage, tendon, retina, peripheral nerve, peripheral nerve sheath, small intestine, large intestine, stomach, skeletal muscle, heart, liver, lung, and kidney.

A thixotropic composition is one where in the absence of shear, the composition has infinite viscosity (it does not move) and in the presence of shear, the composition's viscosity is greatly reduced so as to be deliverable under shear. An example of a thixotropic composition is toothpaste. A phase-changing composition is an aqueous composition which undergoes a change from a liquid to a gel or solid mass based on a suitable trigger such as an increase in temperature, light activation, electromagnetic stimulation, the addition of a phase-changing co-factor (e.g., alginates plus calcium). Such compositions are well known in the art. These compositions are preferably deliverable under injection but also can be delivered topically as necessary. If the viscosity of the composition does not permit conventional injection, high pressure syringes can be used and are well known in the art. Non-limiting examples of such high pressure syringes include those described in U.S. Pat. No. 6,503,244 (incorporated herein by reference in its entirety) and the like.

DETAILED DESCRIPTION OF THE INVENTION

Before this invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

This invention is predicated in part on the discovery that the localized delivery of growth factors can be achieved either using a solution of such growth factors or a suspension of a sufficient amount of modified placental tissue combination with an agent that imparts a sufficient level of solidification in vivo so as to provide for a depot of growth factors to treat a diseased or injured body part.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer is intact or has been substantially removed.

The term "exterior surface" refers to either or both surfaces of the modified placental tissue which will contact the organ of the patient to which tissue is applied.

The term "organ" as used herein is used to have an ordinary meaning in the art, and refers to organs constituting animal viscera in general.

The term "diseased" as used herein refers to an organ and/or body part that is characterized as being in a disease state, or susceptible to being in a disease state, wherein the disease is amenable to treatment with placental growth factors.

The term "injured" as used herein is used to have an ordinary meaning in the art, and includes any and all types of damage to an organ and/or body part, wherein the injury is amenable to treatment with placental growth factors.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "modified placental tissue particles" refers to modified placental tissue particles which have been made into particles small enough to form a suspension suitable for injection through a syringe. Such particles are preferably no more than about 300 microns in size, preferably less than about 250 microns, less than about 200 microns, less than about 150 microns, less than about 100 microns, or less than about 50 microns.

The term "placental growth factors" refers to that array of growth factors obtainable from modified placental tissue. The manner of obtaining such growth factors is not critical to the invention and include, by way of example only, aqueous extraction from the placenta, culturing of placental cells expressing such growth factors, and the like. The concentration of extracted growth factors can be increased by reducing the volume of water, saline, or buffer used to extract the growth factors, by addition of growth factors produced from placental cell cultures, and the like.

The term "sufficient amount" or "therapeutic amount" refers to an amount of placental growth factors that is sufficient to treat an injured or diseased organ or body part. The "sufficient amount" will vary depending on a variety of factors, such as but not limited to, the type and/or amount of placental tissue used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

The term "proximate to" as used herein means adjacent to, or on a body part such that the placental growth factors exert the desired effect. In general, "proximate to" means a distance that is generally within the skill of the art but preferably is within about 3 cm, about 2 cm, about 1 cm of, or on or in the organ or body part.

As used herein, the term "bioerodible," which is used herein interchangeably with the term "biodegradable," refers to a biocompatible material that gradually decomposes, dissolves, hydrolyzes and/or erodes in situ, or that is susceptible to degradation into smaller components or molecules in a living organism over a prolonged period of time, for example, over days or months, such that the material is harmless to the living organism under normal living conditions. Generally, the "bioerodible" polymers herein are polymers that are hydrolyzable, and bioerode in situ primarily through hydrolysis. Preferably, the smaller components or molecules are biocompatible to a patient.

As one of ordinary skill in the art would understand, the degradation of the material results in a continuous release of a therapeutic amount of placental growth factors incorporated in the material over a prolonged period of time, such as about 3 days, about 5 days, about 10 days, about 15 days, about 20 days, about 25 days, about 30 days, about 2 months, about 3 months, about 4 months, about 5 months, or about 6 months. A desired release rate can be determined and/or achieved by adjusting the initial concentration of the growth factors incorporated in the bioerodible or biodegradable mass and the degradation rate of the mass.

Titles or subtitles may be used in the specification for the convenience of a reader, which are not intended to influence the scope of the present invention. Additionally, some terms used in this specification are more specifically defined below.

In one embodiment, placental tissue may be modified as described in U.S. Provisional Application Ser. No. 61/683, 698, including cleaning, separation of the amnion and chorion, removal or maintenance of the epithelial cell layer, decontamination, and dehydration. Dehydration may be accomplished using the drying apparatus as described in U.S. Provisional Application Ser. No. 61/683,698. Both of which applications are incorporated herein by reference in their entireties. Each aspect of that process produces modified placental tissue for the purposes of this invention whether used alone or in combination. However, it is preferred that the modification of placental tissue includes at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration.

In some embodiments of the present technology, the modified placental tissue is selected from amnion, chorion, or both amnion and chorion. In exemplary embodiments, modified placental tissue does not include the umbilical cord.

Modified placental tissue can also be formed into layers which may be dried separately and laminated together or dried together to form multi-layer laminates. Modified placental tissue may also be micronized into particles of a variety of sizes. Micronized placental tissue may be sandwiched between one or more layers of a multilayer laminate, or on top of a laminate. Micronized placental tissue may also be added to a single layer of modified placental tissue. See, for example, U.S. Provisional Application Ser. No. 61/683,700, which is incorporated herein by reference in its entirety.

In some embodiments, localization agents, such as thixotropic agents, phase changing agents, and the like, may include but not limited to, hydrogel, bioerodible, biocompatible polymer, and collagen gels. The presence of one or more localization agents in the compositions of this invention allows the compositions to have certain viscosity such that the compositions are locally retained for a period of time upon administration or injection. It is within the purview of one of ordinary skill in the art to determine the suitable viscosity of the compositions. In some aspects, the compositions have a viscosity between about 5 cP to about $1\times10^8$ cP, or about 5 cP to about $1\times10^6$ cP, or about 5 cP to about $1\times10^5$ cP, or about 5 cP to about $1\times10^4$ cP, or about 5 cP to about $1\times10^3$ cP, or about 6 cP to about 9500 cP at 25° C.

The hydrogels useful in the compositions of this invention can be chemically and/or physically cross-linked hydrogels. In situ chemical cross-linking is obtained, e.g., via photo-initiated, redox-initiated or Michael-type addition polymerization that preferably involve covalent bond formation. Physically cross-linked hydrogels self-assemble under external stimuli and do not rely on covalent bond formation. Temperature, pH, ion concentration, and hydrophobic interactions are certain of the external stimuli useful for such self-assembly and for the immobilization of such hydrogels.

Exemplary polymers suitable for the use in the composition of the present invention include polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, terpolymers and mixtures thereof.

Collagens useful in the present invention include Type I, Type III or Type I+III collagens, for example, alkaline treatment of insoluble collagen extracted from various animals, or by treating with enzyme such as pepsin, trypsin, chymotrypsin, papin or pronase. There are no particular restrictions on the origin of the collagen, and typically collagen can be used that is obtained from the skin, bone, cartilage, tendon or organs, etc. of birds or mammals. Since collagen allows the obtaining of a suitable consistency without heating, preparation can be made easily in the case of gelation. In addition, collagen has a high molecular weight, it more closely resembles living body tissue, has considerable physiological activity, and therefore promotes healing in the case of using on a wound, resulting in a further therapeutic effect in combination with the modified placental tissue. Collagen can be flexible after curing and requires only a short time for crosslinking, in other words, requires only a short time for gelation. Collagen solution can also be made by dissolving in a non-toxic solvent respect to the living body, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or humor, and can demonstrate a high degree of adhesiveness with respect to living body tissue. Collagen solutions used in the present invention can be made at various concentrations, neutralized and prepared for injection. In various aspects, collagen at 0.2 mg/mL, 0.5 mg/mL, 0.75 mg/mL, 1 mg/mL, 2 mg/mL, 3 mg/mL, 4 mg/mL, 5 mg/mL, 6 mg/mL, 7 mg/mL, 8 mg/mL, 10 mg/mL, 20 mg/mL, 30 mg/mL, 40 mg/mL and 50 mg/mL in solution can be used for injection. Upon injection into an organ, chilled collagen gels can thermogel as they reach body temperature or about 37° C.

Other embodiments and uses of the invention will be apparent to those skilled in the art from consideration of the specification and practice of the invention disclosed herein. The specification and examples that follow should be considered exemplary only.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Extraction of Placental Growth Factors

A desired amount of modified placental tissue, which has been previously cleaned, is extracted in 1M NaCl solution at 4° C. at a solution:modified placental tissue ratio of 10:1 (w/w) for 24 hours. Optionally, the extraction is carried out using a rocker platform under agitation. Following extraction, the supernatant is separated from residues by centrifugation. The collected supernatant is then dialyzed against water, and subsequently, the solution containing the placental growth factors is lyophilized. Upon administration, the lyophilized placental growth factors may be reconstituted in water for injection at a predetermined concentration.

Example 2

Preparation of an Immobilized Composition

Five mL of EpiFix® injectible solution containing a suspension of modified placental tissue particles (available from MiMedx Group Inc., Kennesaw, Ga., USA) is cooled to 5° C. To this solution is added approximately 20% w/w of poloxomer PF-127 which is a commercially available polyoxyethylene-polyoxypropylene triblock copolymer of general formula E106 P70 E106, with an average molar mass of 13,000 (25,26). The resulting composition retains its liquid properties at 5° C. but will gelatinate at approximately 20° C.

The cold solution is loaded into a 10 mL syringe and then immediately used to inject the solution into a knee joint of a patient exhibiting a partially torn cartilage. Upon injection, the body temperature causes a phase-transfer to a bioerodable gel which will elute the growth factors during erosion.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A composition comprising a sufficient amount of placental growth factors extracted from modified placental tissue to treat a diseased or injured organ or body part wherein said composition forms a localized bioerodible mass when applied to or proximate to said diseased or injured organ or body part, wherein said composition further comprises micronized placental tissue particles having a particle size of less than 500 µm.

2. The composition of claim 1, further comprising a localization agent.

3. The composition of claim 2, wherein the localization agent is a thixotropic agent, or a phase changing agent.

4. The composition of claim 3, wherein the thixotropic agent is selected from the group consisting of hyaluronic acid, collagen, thrombin gels, fibrin gels and fibrin glues.

5. The composition of claim 3, wherein the phase changing agent is selected from the group consisting of a gel forming agent.

6. The composition of claim 5, wherein the gel forming agent is a copolymer or tripolymer of oxyethylene and oxypropylene units.

7. The composition of claim 2, wherein the localization agent is selected from the group consisting of a hydrogel, a polymer, and a collagen gel.

8. A composition comprising a sufficient amount of placental growth factors extracted from modified placental tissue to treat a diseased or injured organ or body part wherein said composition forms a localized bioerodible mass when applied to or proximate to said diseased or injured organ or body part, wherein said composition further comprises micronized placental tissue particles having a particle size ranging from 25 to 500 µm.

9. The composition of claim 8, wherein the micronized placental tissue particles have a particle size ranging from 25 to 200 µm.

10. A method for preparing a composition for localized delivery of placental growth factors, comprising combining an aqueous mixture of micronized placental tissue particles having a particle size of less than 500 µm and placental growth factors, with a sufficient amount of a localization agent, whereby the composition is locally retained at the site of delivery upon administration.

11. A composition comprising a sufficient amount of placental growth factors extracted from modified placental tissue to treat a diseased or injured organ or body part wherein said composition forms a localized bioerodible mass when applied to or proximate to said diseased or injured organ or body part, wherein said composition further comprises micronized placental tissue particles capable of sieving through an American Standard ASTM sieve of 355-125 µm pore size.

* * * * *